(12) United States Patent
Chang et al.

(10) Patent No.: US 9,976,983 B2
(45) Date of Patent: May 22, 2018

(54) SEMICONDUCTOR ARRANGEMENT AND FORMATION THEREOF

(71) Applicant: Taiwan Semiconductor Manufacturing Company Limited, Hsin-Chu (TW)

(72) Inventors: Yi-Hsien Chang, Shetou Township (TW); Chun-Ren Cheng, Hsin-Chu (TW)

(73) Assignee: Taiwan Semiconductor Manufacturing Company Limited, Hsin-Chu (TW)

(*) Notice: Subject to any disclaimer, the term of this patent is extended or adjusted under 35 U.S.C. 154(b) by 378 days.

(21) Appl. No.: 14/200,148

(22) Filed: Mar. 7, 2014

(65) Prior Publication Data
US 2015/0253283 A1    Sep. 10, 2015

(51) Int. Cl.
| | |
|---|---|
| *G01N 27/447* | (2006.01) |
| *H01L 21/768* | (2006.01) |
| *B81C 1/00* | (2006.01) |
| *B01L 3/00* | (2006.01) |

(52) U.S. Cl.
CPC ...... *G01N 27/447* (2013.01); *B01L 3/502707* (2013.01); *B01L 3/502792* (2013.01); *B81C 1/00126* (2013.01); *B01L 2300/161* (2013.01); *B81B 2203/04* (2013.01); *B81C 2201/0121* (2013.01)

(58) Field of Classification Search
CPC .................. B01L 2400/0427; B01L 3/502792
See application file for complete search history.

(56) References Cited

U.S. PATENT DOCUMENTS

| | | | |
|---|---|---|---|
| 8,268,246 B2* | 9/2012 | Srinivasan | B01L 3/502707 204/643 |
| 2010/0181195 A1* | 7/2010 | Garcia Tello | B01F 13/0071 204/450 |
| 2013/0333762 A1* | 12/2013 | Winger | G05D 7/0629 137/1 |

FOREIGN PATENT DOCUMENTS

WO     WO 2007010041 A1 *   1/2007   ............... G01J 9/02

OTHER PUBLICATIONS

Cho, S., Feb. 2003, "Creating, Transporting, Cutting and Merging Liquid Droplts by Electrowetting-Based Actuation for Digital Microfluidic Circuits," Journal of Micrlelectromechanical Systems, vol. 12, No. , pp. 70-80.

(Continued)

Primary Examiner — Robert Carpenter
(74) Attorney, Agent, or Firm — Cooper Legal Group, LLC

(57) ABSTRACT

A semiconductor arrangement and method of formation are provided. The semiconductor arrangement includes an electro-wetting-on-dielectric (EWOD) device. The EWOD device includes a top portion over a bottom portion and a channel gap between the top portion and the bottom portion. The bottom portion includes a driving dielectric layer over a first electrode, a second electrode and a first separating portion of an ILD layer between the first electrode and a second electrode. The driving dielectric layer has a first thickness less than about 1,000 Å. An EWOD device with a driving dielectric layer having a first thickness less 1000 Å requires a lower applied voltage to alter a shape of a droplet within the device and has a longer operating life than an EWOD device that requires a higher applied voltage to alter the shape of the droplet.

20 Claims, 7 Drawing Sheets

(56) References Cited

OTHER PUBLICATIONS

Cho, S., Fan, S., Moon, Hyejin, and Kim, C., 2002 IEEE, "Towards Digital Microfluidic Circuits: Creating Transporting, Cutting and Merging Liquid Droplets by Electrowetting-Based Actuation," Mechanical and Aerospace Engineering Department, University of California, Los Angeles, CA., pp. 32-35.
Chang, Y., Lee, G., Huang, Fu., Chen, Y., and Lin, J., Integrated Polymerase Chain Reaction Chips Utilizing Digital Microfluids,: Biomed Microdevices 2006, vol. 8, pp. 215-225.

* cited by examiner

SEMICONDUCTOR ARRANGEMENT AND FORMATION THEREOF

BACKGROUND

A semiconductor arrangement comprises one or more semiconductor devices. One type of semiconductor device is an electro-wetting on dielectric (EWOD) device, wherein a shape of a droplet of electrically conductive liquid placed within the device is altered as a function of an electric potential applied across the device.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

Figure 1:
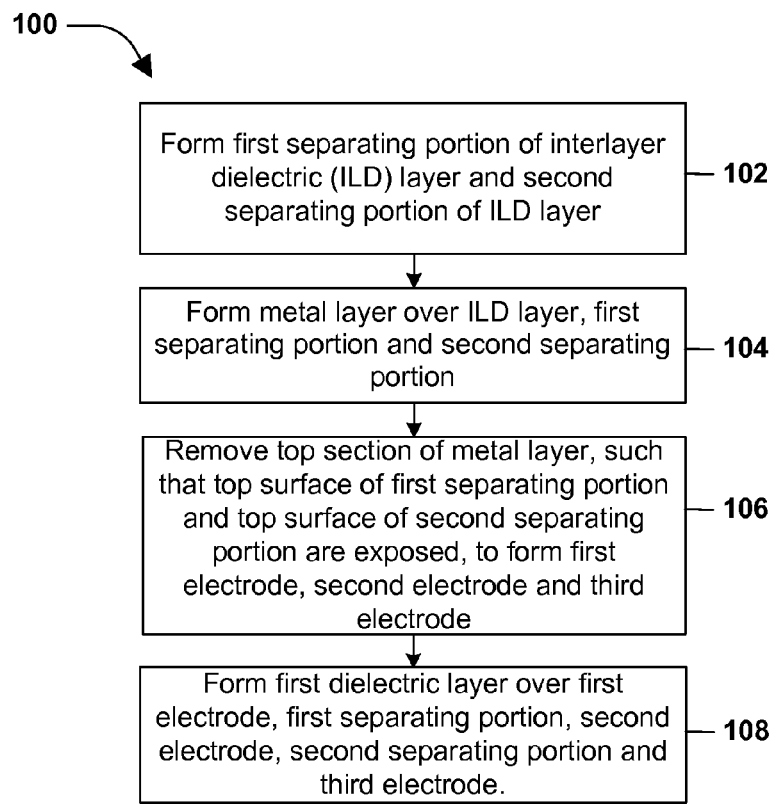
FIG. 1 is a flow diagram illustrating a method of forming a semiconductor arrangement, in accordance with some embodiments.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

One or more techniques for forming a semiconductor arrangement and resulting structures formed thereby are provided herein.

A method 100 of forming a semiconductor arrangement 200 according to some embodiments is illustrated in FIG. 1 and one or more structures formed thereby at various stages of fabrication are illustrated in FIGS. 2-12. According to some embodiments, the semiconductor arrangement 200 comprises a bottom portion 217, a top portion 219 over the bottom portion 217 and a channel gap 228 between the top portion 219 and the bottom portion 217, as illustrated in FIGS. 12a and 12b. In some embodiments, the semiconductor arrangement 200 comprises an electro-wetting-on-dielectric (EWOD) device.

According to some embodiments, the bottom portion 217 comprises a first hydrophobic layer 216a over a driving dielectric layer 214a, the driving dielectric layer 214a over a first electrode 212a, a second electrode 212b and a third electrode 212c in a dielectric layer 202. In some embodiments, a first separating portion 215a is between the first electrode 212a and the second electrode 212b. In some embodiments, a second separating portion 215b is between the second electrode 212b and the third electrode 212c. In some embodiments, the first separating portion 215a has a first width 207a between about 50 nm to about 300 nm and the second separating portion 215b has a second width 207b between about 50 nm to about 300 nm. In some embodiments, the first separating portion 215a has a first separating portion height 225a between about 20 nm to about 800 nm and the second separating portion 215b has a second separating portion height 225b between about 20 nm to about 800 nm. In some embodiments, the first electrode 212a has a first electrode height 227a between about 20 nm to about 800 nm. In some embodiments, the second electrode 212b has a second electrode height 227b between about 20 nm to about 800 nm. In some embodiments, the third electrode 212c has a third electrode height 227c between about 20 nm to about 800 nm. In some embodiments, at least one of the first electrode height 227a, the second electrode height 227b or the third electrode height 227c is equal to at least one of the first separating portion height 225a or the second separating portion height 225b. In some embodiments, a first via 210 connects a metal contact 204 to the first electrode 227a in the dielectric layer 202. In some embodiments, the metal contact 204 is selectively connected to a voltage source 231 by a switch 241. In some embodiments, the driving dielectric layer 214a is over the first electrode 212a, a top surface 209a of the first separating portion 215a, the second electrode 212b, a top surface 209b of the second separating portion 215b and the third electrode 212c. In some embodiments, the driving dielectric layer 214a has a first thickness 211 less than about 1,000 Å.

According to some embodiments, the top portion 219 comprises a second hydrophobic layer 216b over the first hydrophobic layer 216a and separated from the first hydrophobic layer 216a by the channel gap 228. In some embodiments, the top portion 219 further comprises a reference dielectric layer 214b over the second hydrophobic layer 216b, a reference electrode 232 over the reference dielectric layer 214b and a second substrate 222 over the reference electrode 232.

Figure 12A:
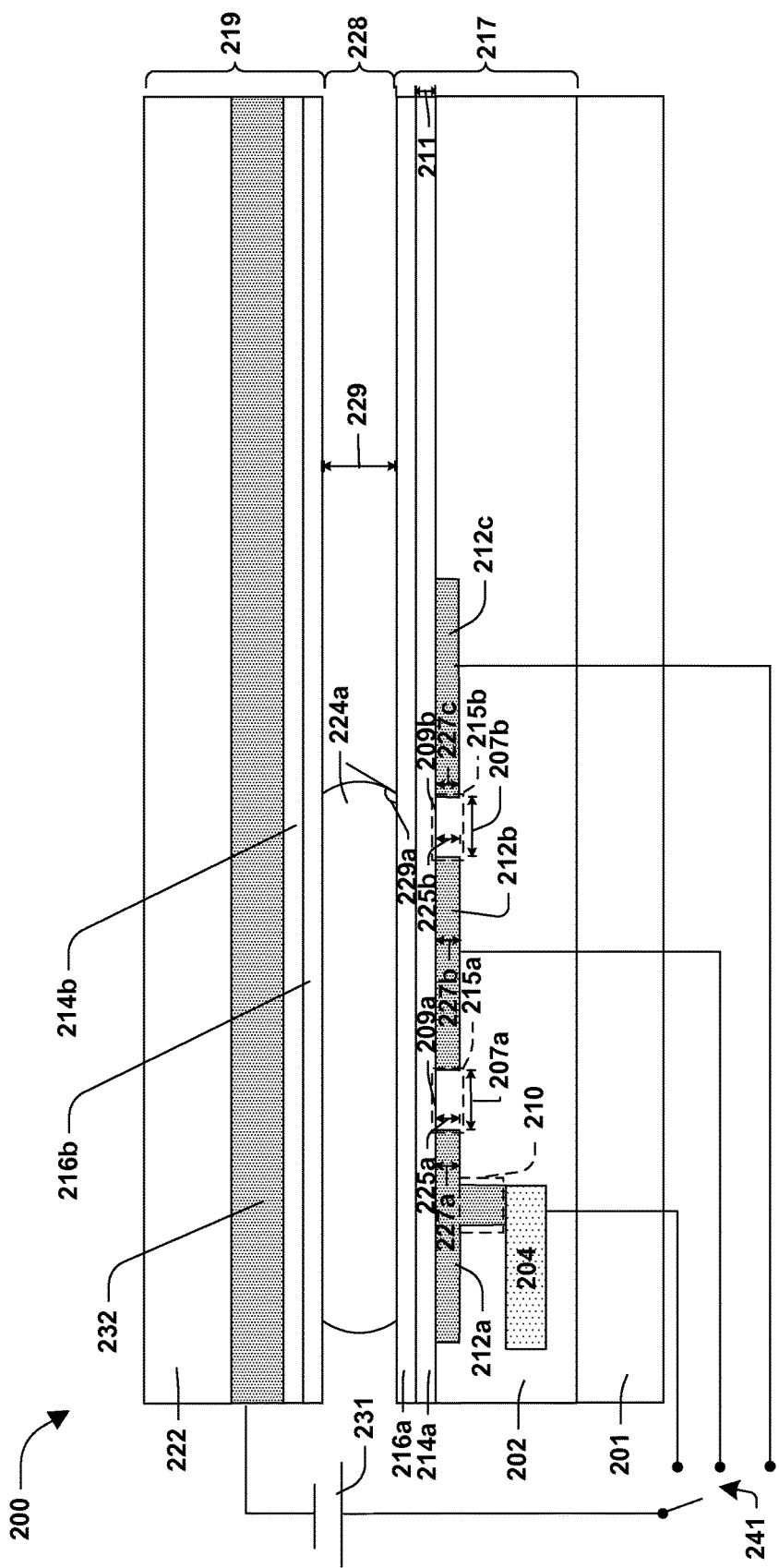
FIG. 12a is an illustration of a semiconductor arrangement, in accordance with some embodiments.

According to some embodiments, a droplet 224 is situated in the channel gap 228 in contact with at least one of the first hydrophobic layer 216a or the second hydrophobic layer 216b. In some embodiments, the first hydrophobic layer 216a is substantially planer. In some embodiments, the channel gap 228 has a channel gap height 229 between about 10 μm (micrometer) to about 100 μm (micrometer). In some embodiments, the EWOD device alters the physical configuration of the droplet 224 on the first hydrophobic layer 216a through the application of a voltage by the voltage source 231. In some embodiments, at least one of the first electrode 212a, the second electrode 212b or the third electrode 212c is selectively coupled to the voltage source 231 by the switch 241. In some embodiments, a probe (not shown) connects the voltage source 231 to the droplet 224 in the channel gap 228. The droplet 224 is shown in two different states, according to some embodiments. In some embodiments, the droplet 224a depicts the droplet 224 when no voltage is applied by the voltage source 231, and the droplet 224a has a first contact angle 229a with respect to the first hydrophobic layer 216a, as illustrated in FIG. 12a. In some embodiments, the droplet 224b depicts the droplet 224 when a voltage is applied by the voltage source 231, and the droplet 224b has a second contact angle 229b with respect to the first hydrophobic layer 216a, as illustrated in 12b. In some embodiments, the change in the contact angle is caused by the applied voltage according to equation (1) below.

$$\cos\theta_v - \cos\theta_o = \frac{\varepsilon\varepsilon_o}{2\gamma_{LG}t}V^2$$

In equation (1), V is the applied electrical potential or voltage, $\theta_v$ is the second contact angle 229b under applied voltage V, and $\theta_o$ is the first contact angle 229a without the applied voltage V. Other variables include: $\varepsilon$, the dielectric constant of the driving dielectric layer 214a; $\varepsilon_0$, the vacuum permittivity; $2\gamma_{LG}$, the surface tension; and t, the first thickness 211 of the driving dielectric layer 214a. In some embodiments, the greater the first thickness 211 of the driving dielectric layer 214a, the greater the applied voltage required to alter the contact angle of the droplet 224. In some embodiments, a lesser first thickness 211, such as a first thickness less than 1,000 Å of the driving dielectric layer 214a requires a lower applied voltage than a dialectic layer having a greater first thickness. In some embodiments, a higher dielectric constant of the driving dielectric layer 214a requires a lower applied voltage than a dielectric layer having a lower dielectric constant. In some embodiments, an EWOD device that requires a lower applied voltage, such as an applied voltage between about 5v to about 200v, has a longer operating life than an EWOD device that requires a higher applied voltage, such as an applied voltage between about 200v to about 500v. In some embodiments, an EWOD device with a substantially planer first hydrophobic layer 216a has an increased flow rate of the droplet 224 as compared to an EWOD device that lacks a substantially planer first hydrophobic layer. Further, the substantially planer hydrophobic layer 216a reduces the voltage required to alter the contact angle of the droplet 224, due to less surface resistance, as compared to a voltage required to alter the contact angel of a droplet on a first hydrophobic layer that is not substantially planer, according to some embodiments.

Figure 2:
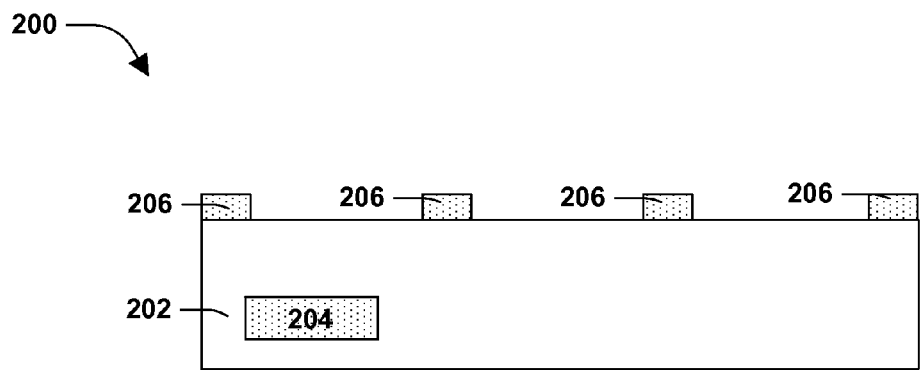
FIG. 2 is an illustration of a semiconductor arrangement, in accordance with some embodiments.
Figure 3:
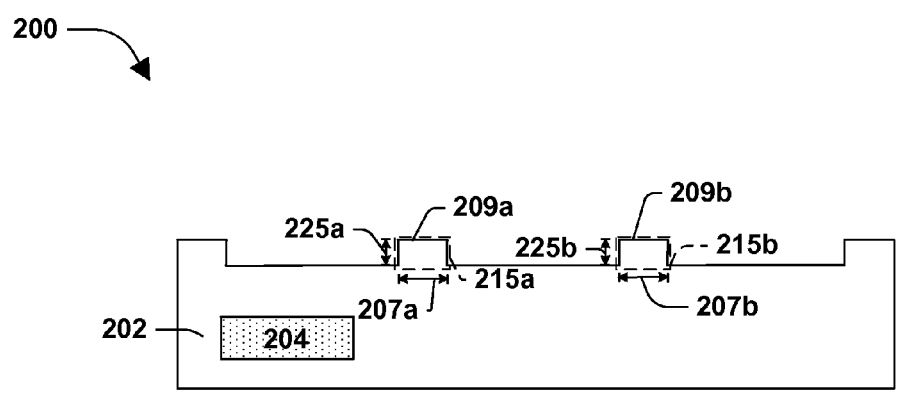
FIG. 3 is an illustration of a semiconductor arrangement, in accordance with some embodiments.
Figure 4:
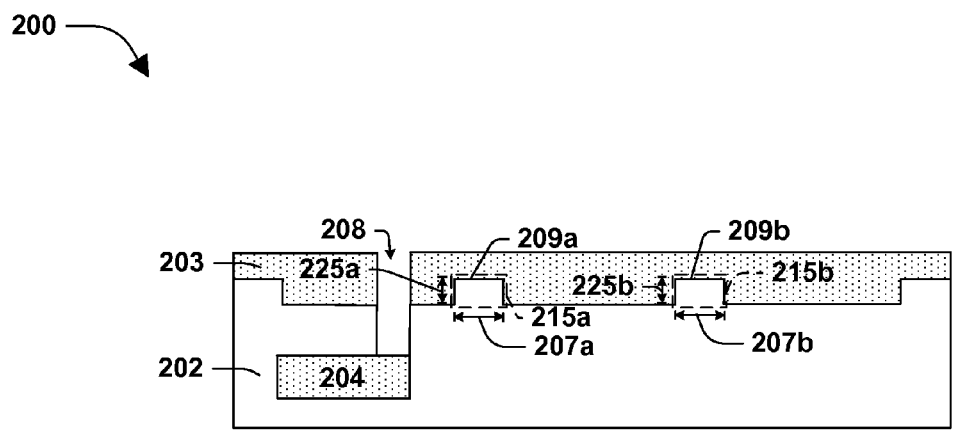
FIG. 4 is an illustration of a semiconductor arrangement, in accordance with some embodiments.
Figure 5:
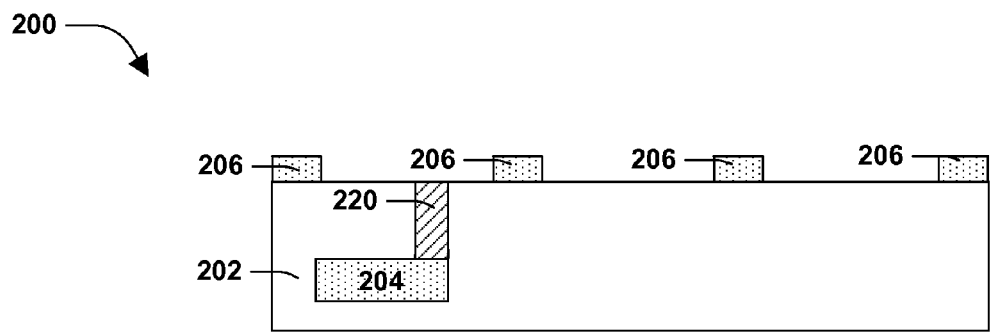
FIG. 5 is an illustration of a semiconductor arrangement, in accordance with some embodiments.
Figure 6:
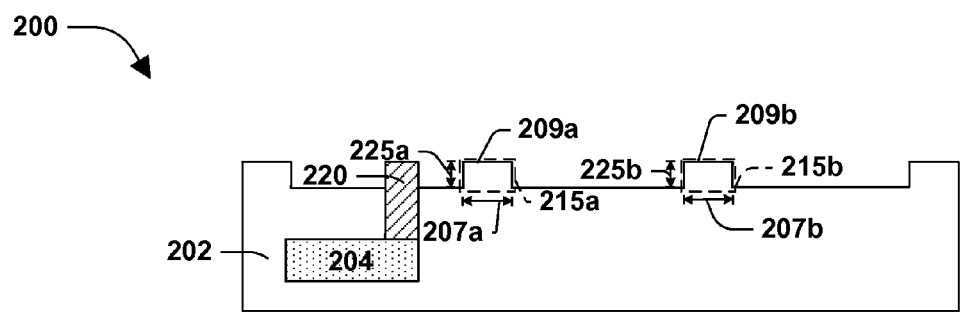
FIG. 6 is an illustration of a semiconductor arrangement, in accordance with some embodiments.
Figure 7:
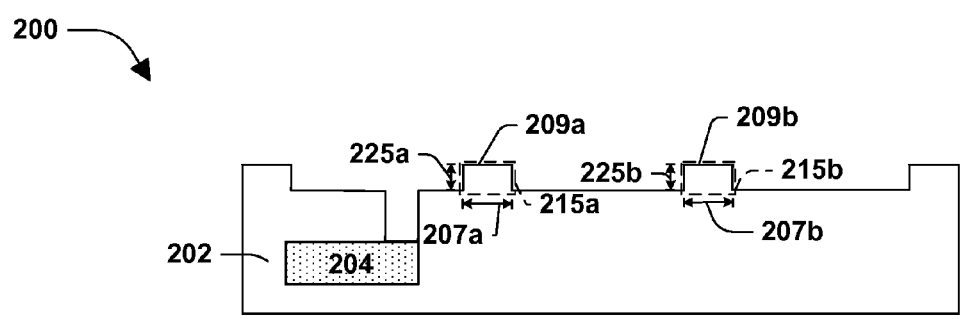
FIG. 7 is an illustration of a semiconductor arrangement, in accordance with some embodiments.
Figure 12B:
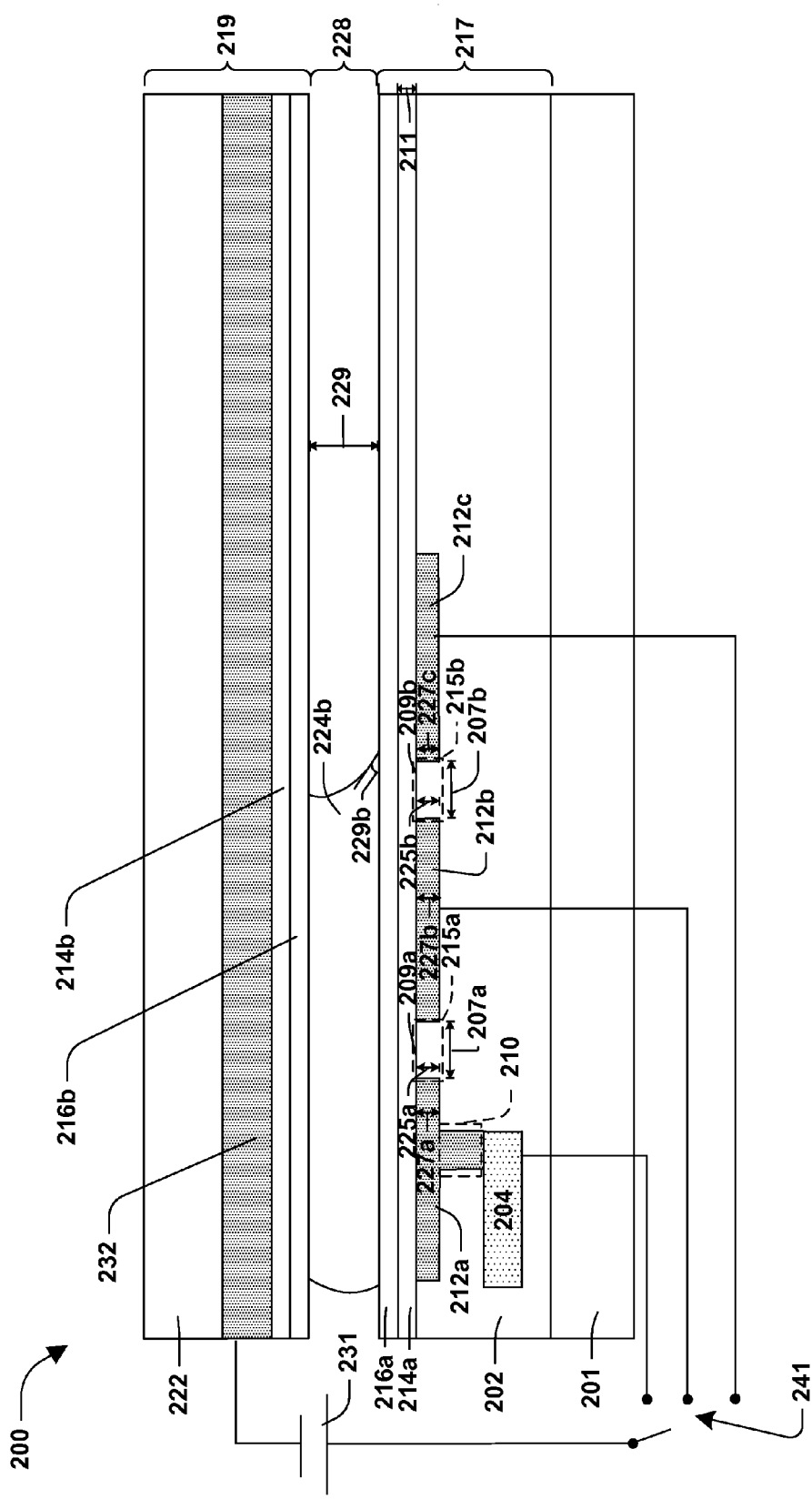
FIG. 12b is an illustration of a semiconductor arrangement, in accordance with some embodiments.

At 102, the first separating portion 215a of the dielectric layer 202 and the second separating portion 215b of the dielectric layer 202 are formed, as illustrated in FIGS. 3 and 6, according to some embodiments. Turning to FIG. 2, prior to FIG. 3, the dielectric layer 202 is over a first substrate 201, as illustrated in FIGS. 12a and 12b, according to some embodiments. According to some embodiments, the first substrate 201 comprises at least one of an epitaxial layer, a silicon-on-insulator (SOI) structure, a silicon wafer, a glass wafer, a quartz wafer or a die formed from a wafer. In some embodiments, the first substrate 201 comprises at least one of a transistor, capacitor, or other IC devices, such as a CMOS device. In some embodiments, the dielectric layer 202 comprises at least one of a high dielectric constant material or a medium dielectric constant material. In some embodiments, the dielectric layer 202 comprises at least one of an inter layer dielectric or an inter metal dielectric. In some embodiments, a first photoresist 206 is formed over the dielectric layer 202 and patterned such that the first separating portion 215a and the second separating portion 215b are formed from portions of the dielectric layer 202 under patterned portions of the first photoresist (or etching mask) 206, such as by etching away portions of the dielectric layer 202 not under patterned portions of the first photoresist 206. Once the separating portions are formed the patterned first photoresist 206 is removed, as illustrated in FIG. 3. In some embodiments, the metal contact 204 is in the dielectric layer 202. In some embodiments, the first separating portion 215a has the first width 207a between about 50 nm to about 300 nm and the second separating portion 215b has the second width 207b between about 50 nm to about 300 nm. In some embodiments, the first separating portion 215a has the first separating portion height 225a between about 20 nm to about 800 nm and the second separating portion 215b has the second separating portion height 225b between about 20 nm to about 800 nm. In some embodiments, a second photoresist 203 is formed over the dielectric layer 202, such that a top surface of the dielectric layer 202 is exposed over the metal contact 204, as illustrated in FIG. 4. In some embodiments, a first opening 208 is formed, such as by etching, such that a top surface of the metal contact 204 is exposed. In some embodiments, the second photoresist 203 is removed. Turning to FIG. 5, prior to FIG. 6, the dielectric layer 202 comprises substantially the same composition as described above with regards to the dielectric layer 202, as illustrated in FIG. 2, according to some embodiments. In some embodiments, the first photoresist 206 is formed over portions of the dielectric layer 202, such that the first separating portion 215a and the second separating portion 215b are formed under the first photoresist 206. In some embodiments, the first separating portion 215a and the second separating portion 215b are formed in substantially the same manner as described above with regards to the first separating portion 215a and the second separating portion 215b as illustrated in FIG. 4. In some embodiments, the metal contact 204 is in the dielectric layer 202. In some embodiments, a sacrificial via 220 is over the metal contact 204 in the dielectric layer 202, where the sacrificial via 220 has a different etch selectivity relative to the dielectric layer 202 and thus is not etched or is etched very little, as illustrated in FIG. 6, when the dielectric layer 202 is etched to form the separating portions. In some embodiments, the first opening 208 is subsequently formed by removing the first sacrificial via 220, such that the top surface of the metal contact 204 is exposed, as illustrated in FIG. 7.

Figure 8:
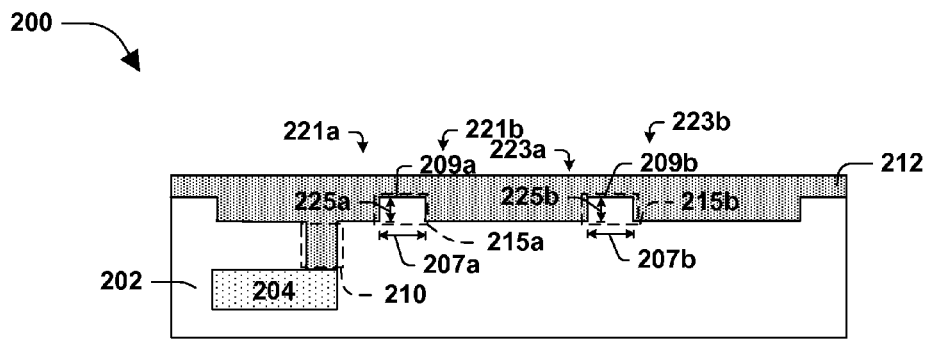
FIG. 8 is an illustration of a semiconductor arrangement, in accordance with some embodiments.

At 104, a metal layer 212 is formed over the dielectric layer 202, the first separating portion 215a and the second separating portion 215b, as illustrated in FIG. 8, according to some embodiments. In some embodiments, the first metal layer 212 comprises at least one of tungsten or copper. In some embodiments, the first metal layer 212 is formed by at least one of atomic layer deposition, physical vapor deposition or chemical vapor deposition. In some embodiments, the metal layer 212 is formed in the first opening 208 to form a first via 210, the first via 210 connected to the metal contact 204.

Figure 9:
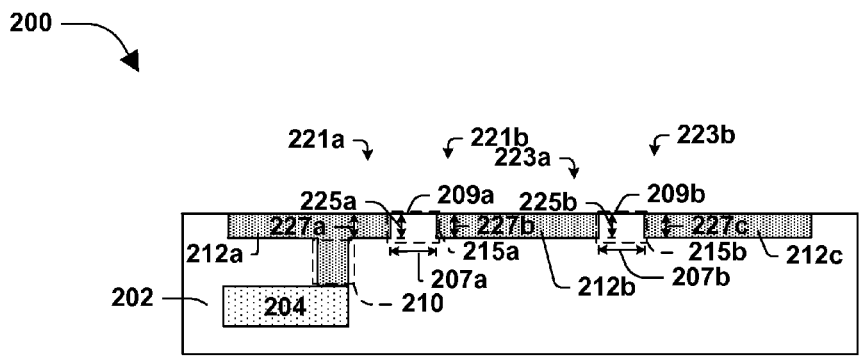
FIG. 9 is an illustration of a semiconductor arrangement, in accordance with some embodiments.

At 106, a top section of the metal layer 212 is removed, such that the top surface 209a of the first separating portion 215a and the top surface 209b of the second separating portion 215b are exposed, as illustrated in FIG. 9, according to some embodiments. In some embodiments, the first electrode 212a is formed from the metal layer 212 on a first side 221a of the first separating portion 215a and the second electrode 212b is formed from the metal layer 212 on a second side 221b of the first separating portion 215a. In some embodiments, the third electrode 212c is formed from the metal layer 212 on a second side 223b of the second separating portion 215b, such that the second electrode 212b is on a first side 223a of the second separating portion 215b. In some embodiments, the first electrode 212a has the first electrode height 227a between about 20 nm to about 800 nm. In some embodiments, the second electrode 212b has the second electrode height 227b between about 20 nm to about 800 nm. In some embodiments, the third electrode 212c has the third electrode height 227c between about 20 nm to about 800 nm. In some embodiments, at least one of the first electrode height 227a, the second electrode height 227b or the third electrode height 227c is equal to at least one of the first separating portion height 225a or the second separating portion height 225b. In some embodiments, the top section of the metal layer 212 is removed by chemical mechanical planarization (CMP). In some embodiments, the CMP has a high selectivity for copper/tungsten to dielectric, such that the CMP removes little to none of the first separating portion 215a or the second separating portion 215b. According to some embodiments, since the first electrode 212a, the second electrode 212b and the third electrode 212c are essentially formed within recesses within the dielectric layer 202, where such recesses are defined by or adjacent to the first separating portion 215a and the second separating portion 215b, the first electrode 212a, the second electrode 212b and the third electrode 212c are substantially coplanar or flush with the first separating portion 215a and the second separating portion 215b. According to some embodiments, this planar arrangement allows layers formed thereover to be substantially planar.

Figure 10:
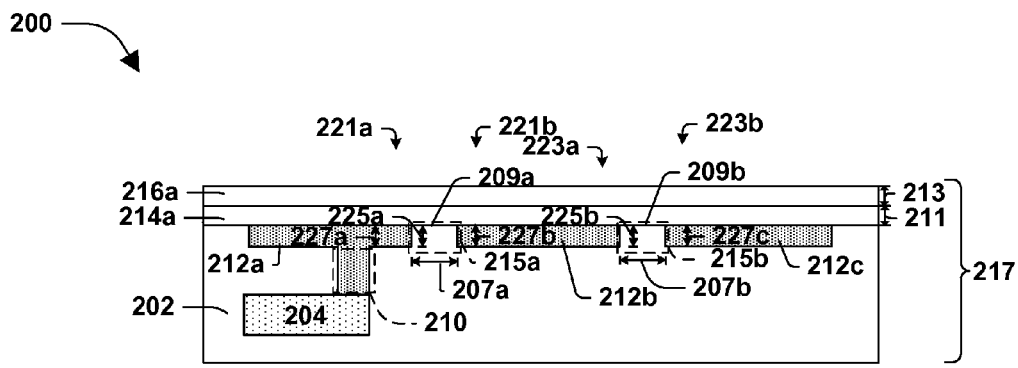
FIG. 10 is an illustration of a semiconductor arrangement, in accordance with some embodiments.
Figure 11:
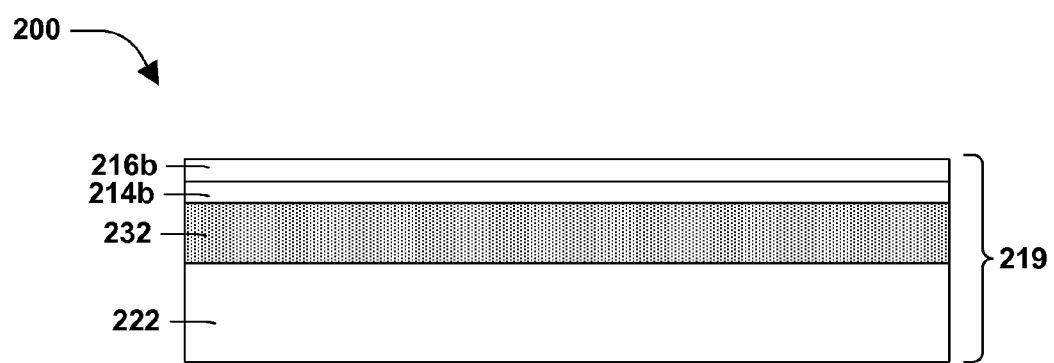
FIG. 11 is an illustration of a semiconductor arrangement, in accordance with some embodiments.

At 108, the driving dielectric layer 214a is formed over the first electrode 212a, the first separating portion 215a, the second electrode 212b, the second separating portion 215b and the third electrode 212c, as illustrated in FIG. 10, according to some embodiments. In some embodiments, the driving dielectric layer 214a has the first thickness 211 less than about 1,000 Å. In some embodiments, the driving dielectric layer 214a is formed by at least one of atom layer deposition, chemical vapor deposition or physical vapor deposition. In some embodiments, the driving dielectric layer 214a comprises a high dielectric constant material, such as silicon oxide, hafnium silicate, hafnium oxide, zirconium oxide, aluminum oxide, tantalum pentoxide, hafnium dioxide-alumina ($Hf_{O2}$-$A_{l2O3}$) alloy, Barium strontium titanate (BST), or combinations thereof. In some embodiments, the driving dielectric layer 214a has few to no seams or other defects due to the CMP being performed on the metal layer 212, rather than on the driving dielectric layer 214a. In some embodiments, the first hydrophobic layer 216a is formed over the driving dielectric layer 214a to form the bottom portion 217. In some embodiments, the first hydrophobic layer 216a has a substantially planer top surface given that the driving dielectric layer 214a is likewise substantially planar due to being formed over the planar arrangement of the first, second and third electrodes and the first and second separating portions. In some embodiments, the first hydrophobic layer 216a comprises at least one of polytetrafluoroethylene or a self assembled monolayer. In some embodiments, the first hydrophobic layer 216a has a first hydrophobic thickness 213 between about 30 Å to about 1000 Å. In some embodiments, the top portion 219, as illustrated in FIG. 11 is inverted and placed over the bottom portion 217, as illustrated in FIGS. 12a and 12b, such that the channel gap 228 is formed between the top portion 219 and the bottom portion 217. According to some embodiments, the top portion 219 comprises the second hydrophobic layer 216b over the first hydrophobic layer 216a and is separated by the channel gap 228. In some embodiments, the top portion 219 further comprises the reference dielectric layer 214b over the second hydrophobic layer 216b, the reference electrode 232 over the reference dielectric layer 214b and the second substrate 222 over the reference electrode 232. In some embodiments, the second hydrophobic layer 216b comprises at least one of polytetrafluoroethylene or a self assembled monolayer. In some embodiments, the second substrate 222 comprises silicon. In some embodiments, the greater the first thickness 211 of the driving dielectric layer 214a, the greater the applied voltage required to alter the contact angle of the droplet 224. In some embodiments, a lesser first thickness 211 requires a lower applied voltage to alter the contact angle of the droplet 224. In some embodiments, a EWOD device that requires a lower applied voltage, such as an applied voltage between about 15v to about 200v, to alter the contact angle of the droplet 224 has a longer operating life than an EWOD device that requires a higher applied voltage, such as an applied voltage between about 200v to about 500v, to alter the contact angle of the droplet 224. In some embodiments, the driving dielectric layer 214a has few to no seams or other defects due to the CMP being performed on the metal layer 212 as opposed to performing CMP on the driving dielectric layer 214a. In some embodiments, the EWOD device with the substantially planer first hydrophobic layer 216a has an increased flow rate of the droplet 224 as compared to an EWOD device that lacks a substantially planer first hydrophobic layer. Further, the substantially planer hydrophobic layer 216a reduces the voltage required to alter the contact angle of the droplet 224, due to less surface resistance, as compared to a voltage required to alter the contact angel of a droplet on a first hydrophobic layer that is not substantially planer, according to some embodiments.

According to some embodiments, a semiconductor arrangement comprises a first electrode adjacent a second electrode in a dielectric layer, the first electrode separated from the second electrode by a first separating portion of the dielectric layer. In some embodiments, the dielectric layer is formed over a first substrate. In some embodiments, a driving dielectric layer is over and in contact with the first electrode, the second electrode and the first separating portion.

According to some embodiments, a method of forming a semiconductor arrangement comprises forming a first separating portion of a dielectric layer, the dielectric layer formed over a first substrate and forming a metal layer over the dielectric layer and the first separating portion. According to some embodiments, a method of forming a semiconductor arrangement further comprises removing a top section of the metal layer, such that a top surface of the first separating portion is exposed and a first electrode is formed from the metal layer on a first side of the first separating portion and a second electrode is formed from the metal layer on a second side of the first separating portion and forming a driving dielectric layer over the first electrode, the first separating portion and the second electrode.

According to some embodiments, a semiconductor arrangement comprises a top portion over a bottom portion and a channel gap between the top portion and the bottom portion. In some embodiments, the bottom portion comprises a first electrode adjacent a second electrode in a dielectric layer, the first electrode separated from the second electrode by a first separating portion of the dielectric layer, the dielectric layer formed over a substrate. In some embodiments, a driving dielectric layer is over and in contact with the first electrode, the second electrode and the first separating portion and a first hydrophobic layer over the driving dielectric layer. In some embodiments, the top portion comprises a second hydrophobic layer over and separated from the first hydrophobic layer by a channel gap, a reference dielectric layer over the second hydrophobic layer and a reference electrode over a second dielectric layer.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

Various operations of embodiments are provided herein. The order in which some or all of the operations are described should not be construed to imply that these operations are necessarily order dependent. Alternative ordering will be appreciated having the benefit of this description. Further, it will be understood that not all operations are necessarily present in each embodiment provided herein. Also, it will be understood that not all operations are necessary in some embodiments.

It will be appreciated that layers, features, elements, etc. depicted herein are illustrated with particular dimensions relative to one another, such as structural dimensions or orientations, for example, for purposes of simplicity and ease of understanding and that actual dimensions of the same differ substantially from that illustrated herein, in some embodiments. Additionally, a variety of techniques exist for forming the layers features, elements, etc. mentioned herein, such as etching techniques, implanting techniques, doping techniques, spin-on techniques, sputtering techniques such as magnetron or ion beam sputtering, growth techniques, such as thermal growth or deposition techniques such as chemical vapor deposition (CVD), physical vapor deposition (PVD), plasma enhanced chemical vapor deposition (PECVD), or atomic layer deposition (ALD), for example.

Moreover, "exemplary" is used herein to mean serving as an example, instance, illustration, etc., and not necessarily as advantageous. As used in this application, "or" is intended to mean an inclusive "or" rather than an exclusive "or". In addition, "a" and "an" as used in this application and the appended claims are generally be construed to mean "one or more" unless specified otherwise or clear from context to be directed to a singular form. Also, at least one of A and B and/or the like generally means A or B or both A and B. Furthermore, to the extent that "includes", "having", "has", "with", or variants thereof are used, such terms are intended to be inclusive in a manner similar to the term "comprising". Also, unless specified otherwise, "first," "second," or the like are not intended to imply a temporal aspect, a spatial aspect, an ordering, etc. Rather, such terms are merely used as identifiers, names, etc. for features, elements, items, etc. For example, a first element and a second element generally correspond to element A and element B or two different or two identical elements or the same element.

Also, although the disclosure has been shown and described with respect to one or more implementations, equivalent alterations and modifications will occur to others skilled in the art based upon a reading and understanding of this specification and the annexed drawings. The disclosure comprises all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure. In addition, while a particular feature of the disclosure may have been disclosed with respect to only one of several implementations, such feature may be combined with one or more other features of the other implementations as may be desired and advantageous for any given or particular application.

What is claimed is:

1. A semiconductor arrangement comprising:
   a first substrate;
   a dielectric layer over the first substrate, wherein a surface of the dielectric layer interfaces with a surface of the first substrate;
   a metal contact having a bottom surface in contact with the dielectric layer and a top surface in contact with the dielectric layer;
   a first electrode and a second electrode in the dielectric layer, wherein:
      the first electrode is separated from the second electrode by a first separating portion of the dielectric layer, and
      a via extends between the metal contact and the first electrode to electrically couple the first electrode to the metal contact; and
   a driving dielectric layer over and in contact with the first electrode, the second electrode and the first separating portion.

2. The semiconductor arrangement of claim 1, the driving dielectric layer having a first thickness less than about 1,000 Å.

3. The semiconductor arrangement of claim 1, comprising:
   a first hydrophobic layer over the driving dielectric layer.

4. The semiconductor arrangement of claim 3, the first hydrophobic layer comprising at least one of polytetrafluoroethylene or a self assembled monolayer.

5. The semiconductor arrangement of claim 3, comprising:
a second hydrophobic layer over the first hydrophobic layer, wherein the second hydrophobic layer is separated from the first hydrophobic layer by a channel gap.

6. The semiconductor arrangement of claim 5, comprising:
a reference dielectric layer over the second hydrophobic layer; and
a reference electrode over the reference dielectric layer.

7. The semiconductor arrangement of claim 1, wherein the first electrode has a first width and the metal contact has a second width less than the first width.

8. The semiconductor arrangement of claim 1, comprising:
a switch coupled to the bottom surface of the metal contact through the first substrate.

9. The semiconductor arrangement of claim 8, wherein:
the switch is configured to selectively couple the first electrode and the second electrode to a voltage source.

10. The semiconductor arrangement of claim 1, the first separating portion having a first width between about 50 nm to about 300 nm.

11. A semiconductor arrangement comprising:
a bottom portion, the bottom portion comprising:
a first substrate;
a dielectric layer over the first substrate, wherein a surface of the dielectric layer interfaces with a surface of the first substrate;
a metal contact in the dielectric layer, wherein the metal contact has a first width;
a first electrode and a second electrode in the dielectric layer, wherein:
the first electrode has a second width greater than the first width,
the first electrode is separated from the second electrode by a first separating portion of the dielectric layer, and
a via extends between the metal contact and the first electrode to electrically couple the first electrode to the metal contact;
a driving dielectric layer over and in contact with the first electrode, the second electrode and the first separating portion; and
a first hydrophobic layer over the driving dielectric layer; and
a top portion, the top portion comprising:
a second hydrophobic layer over and separated from the first hydrophobic layer by a channel gap;
a reference dielectric layer over the second hydrophobic layer; and
a reference electrode over the reference dielectric layer.

12. The semiconductor arrangement of claim 11, the driving dielectric layer having a first thickness less than about 1,000 Å.

13. The semiconductor arrangement of claim 11, wherein:
the first electrode has a first electrode height and the second electrode has a second electrode height; and
the first separating portion has a first separating portion height, at least one of the first electrode height or the second electrode height equal to the first separating portion height.

14. A semiconductor arrangement comprising:
a hydrophobic layer defining a first surface of a fluidic channel gap;
a driving dielectric layer underlying the hydrophobic layer;
a first set of electrodes underlying the driving dielectric layer;
a dielectric layer underlying the driving dielectric layer, underlying the first set of electrodes, and further disposed between a first electrode of the first set of electrodes and a second electrode of the first set of electrodes;
a metal contact underlying the first electrode, wherein the metal contact is electrically coupled to the first electrode by a via extending through the dielectric layer; and
a substrate underlying the dielectric layer and interfacing with the dielectric layer, wherein the metal contact is spaced apart from the substrate by the dielectric layer.

15. The semiconductor arrangement of claim 14, wherein a top surface of the first electrode, a top surface of the second electrode, and a top surface of the dielectric layer are in contact with the driving dielectric layer.

16. The semiconductor arrangement of claim 14, wherein a k-value of the driving dielectric layer is greater than a k-value of the dielectric layer.

17. The semiconductor arrangement of claim 14, comprising:
a second hydrophobic layer defining a second surface of a fluidic channel gap;
a reference dielectric layer overlying the second hydrophobic layer; and
a reference electrode overlying the reference dielectric layer.

18. The semiconductor arrangement of claim 17, wherein the reference electrode overlies the first electrode and the second electrode.

19. The semiconductor arrangement of claim 17, comprising a voltage source, wherein a first terminal of the voltage source is coupled to the reference electrode and a second terminal of the voltage source is selectively coupled to first electrode and the second electrode.

20. The semiconductor arrangement of claim 14, wherein a top surface of the dielectric layer is co-planar with a top surface of the first electrode and a top surface of the second electrode.

* * * * *